(12) United States Patent
Zeng et al.

(10) Patent No.: US 12,343,035 B2
(45) Date of Patent: Jul. 1, 2025

(54) NEEDLE GUIDING BRACKET WITH ADJUSTABLE ANGLES

(71) Applicant: JingFang Precision Medical Device (Shenzhen) Co., Ltd., Guangdong (CN)

(72) Inventors: Weihua Zeng, Guangdong (CN); Junhua Zeng, Guangdong (CN); Sheng Xia, Guangdong (CN)

(73) Assignee: JingFang Precision Medical Device (Shenzhen) Co., Ltd., Shenzhen (CN)

(*) Notice: Subject to any disclaimer, the term of this patent is extended or adjusted under 35 U.S.C. 154(b) by 471 days.

(21) Appl. No.: 17/781,866

(22) PCT Filed: Jan. 3, 2020

(86) PCT No.: PCT/CN2020/070308
§ 371 (c)(1),
(2) Date: Jun. 2, 2022

(87) PCT Pub. No.: WO2021/114442
PCT Pub. Date: Jun. 17, 2021

(65) Prior Publication Data
US 2023/0000519 A1    Jan. 5, 2023

(30) Foreign Application Priority Data

Dec. 10, 2019  (CN) .......................... 201911261921.5
Dec. 10, 2019  (CN) .......................... 201922208638.2

(51) Int. Cl.
*A61B 17/34*  (2006.01)

(52) U.S. Cl.
CPC .. *A61B 17/3403* (2013.01); *A61B 2017/3405* (2013.01); *A61B 2017/3413* (2013.01)

(58) Field of Classification Search
CPC ........ A61B 8/033–085; A61B 17/3403; A61B 2017/3405–3413
See application file for complete search history.

(56) References Cited

U.S. PATENT DOCUMENTS 5,941,889 A      8/1999  Cermak
2010/0041990 A1* 2/2010  Schlitt ............... A61B 17/3403
                                              600/461

FOREIGN PATENT DOCUMENTS

CN    105455883 A  *  4/2016  ......... A61B 17/3403
CN    208355536 U  *  1/2019

OTHER PUBLICATIONS

International Search Report of PCT Patent Application No. PCT/CN2020/070308 issued on Aug. 27, 2020.

* cited by examiner

*Primary Examiner* — Elizabeth Houston
*Assistant Examiner* — Jonathan A Hollm

(57) ABSTRACT

A needle guiding bracket with adjustable angles is provided, comprising a bracket body, a mounting base, and an angle block; the angle block and the mounting base are rotationally connected at corresponding first ends, and a cooperating limiting structure is provided between the angle block and the mounting base to enable the angle block and the mounting base to only relatively rotate; a second end of the angle block is provided with at least one elastic arm having raised positioning platforms; a second end of the mounting base is provided with at least one group of angle gear grooves for the raised positioning platforms to be embedded therein; and the angle block is further provided with an elastic element which applies elastic force to the elastic arms so as to enable the raised positioning platforms to be embedded within the angle gear grooves.

6 Claims, 5 Drawing Sheets

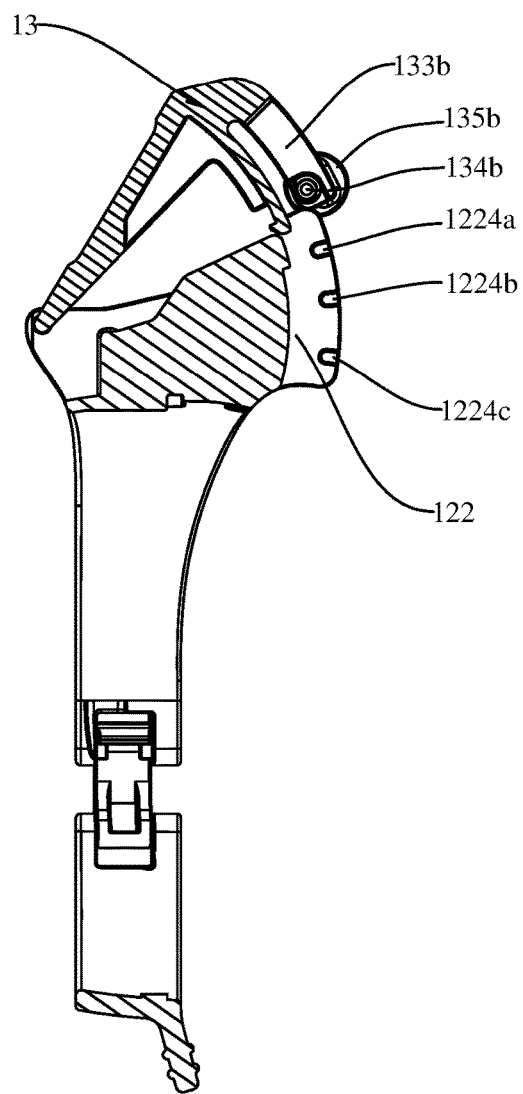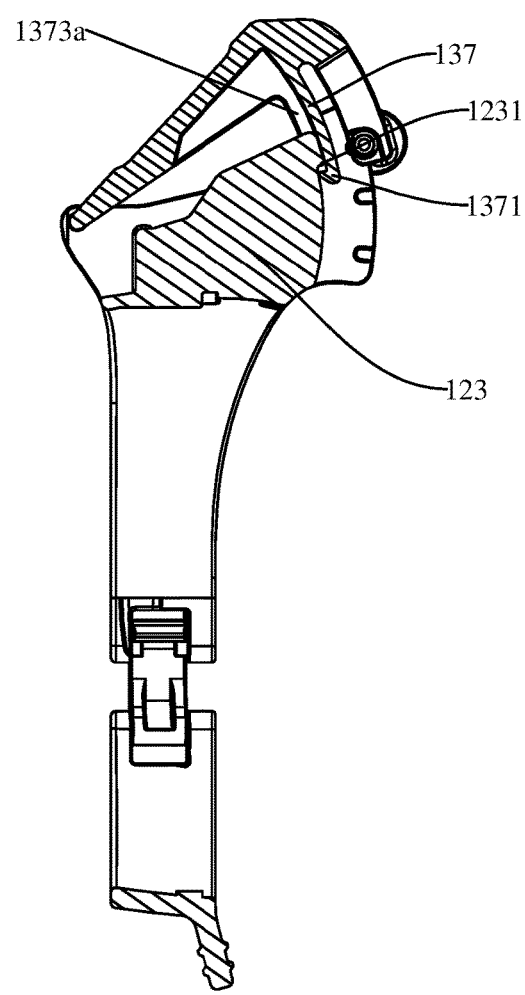
FIG. 4
FIG. 5

NEEDLE GUIDING BRACKET WITH ADJUSTABLE ANGLES

FIELD

The present application generally relates to medical instruments, more particularly to a needle guiding bracket with adjustable angles.

BACKGROUND

At present, ultrasonic interventional diagnosis and treatment need to configure a needle guiding bracket for an ultrasound probe. The needle guiding bracket is generally installed on the ultrasound probe as a reusable part, and then covered with a sterile probe cover, and then doing biopsy operation with biopsy needle consumables. Generally, the needle guiding bracket provides more than two needle guiding angles. When the depth of the lesion is different, interventional operations with different biopsy depths can be realized by changing the needle guiding angle, so the needle guiding bracket must have function of adjusting the needle guiding angles.

The needle guiding bracket can be metal or plastic, but the plastic material is commonly used, which is easy to facilitate snap and fasten with the ultrasound probe. The prior angle adjustment method of the plastic needle guiding bracket is disclosed in U.S. Pat. No. 5,941,889 titled "Multiple angle disposable needle guide system", in which a plurality of angle grooves are arranged on a bracket body, and an angle block is connected to the bracket body by a metal pin and can be rotated with the metal pin as a rotation axis, and a metal rod is also installed on the angle block, and the angle block is fixed by the metal rob being buckled into the angle groove. However, this product has a complex structure with many parts, needs long assembly process, and it is complicated for angle adjustment and positioning operation.

SUMMARY

The technical problem to be solved by the present application is to provide a needle guiding bracket with adjustable angles that has more simple structure and more convenient angle adjustment operation in view of the above-mentioned drawbacks of the prior art.

The technical solution adopted by the present application to solve the technical problem thereof is to provide a needle guiding bracket with adjustable angles, comprising a bracket body configured to cooperatively mounting with an ultrasound probe, a mounting base arranged on the bracket body, and an angle block rotationally connected with the mounting base, wherein the angle block and the mounting base are rotationally connected at corresponding first ends, and a corresponding limiting structure is provided between the angle block and the mounting base to enable the angle block and the mounting base to only rotate relative to each other, and the angle block is also provided with configurations for mounting a needle guide or directly forming a needle tract, and wherein a second end of the angle block opposite to the first end is provided with at least one elastic arm, and a raised positioning platform extending perpendicular to a rotation plane of the angle block is provided on the elastic arm; a corresponding second end of the mounting base is provided with at least one group of angle gear grooves that cooperates with the raised positioning platform of the at least one elastic arm for the raised positioning platform to be embedded therein such that a fixed angle is formed between the angle block and the mounting base; and the angle block is further provided with an elastic element which applies elastic force to the elastic arm to urge the raised positioning platform to be embedded within the angle gear grooves.

In the needle guiding bracket with adjustable angles according to an embodiment of the present application, the mounting base comprises a first limiting plate and a second limiting plate, and the first end of the angle block is rotationally connected between the first ends of the first limiting plate and the second limiting plate.

In the needle guiding bracket with adjustable angles according to an embodiment of the present application, a first elastic sheet and a second elastic sheet extend from the first ends of the first limiting plate and the second limiting plate respectively, with the first elastic sheet and the second elastic sheet being correspondingly provided with a first mounting hole and a second mounting hole, and two outer sides of the first end of the angle block are respectively provided with a first rotating shaft and a second rotating shaft which are installed into the first mounting hole and the second mounting hole.

In the needle guiding bracket with adjustable angles according to an embodiment of the present application, a first rotating matching surface and a second rotating matching surface are respectively provided on both sides of the angle block, and the first rotating matching surface and the second rotating mating surface respectively cooperate with an inner surface of the first limiting plate and an inner surface of the second limiting plate to limit the angle block and the mounting base to only rotate relative to each other.

In the needle guiding bracket with adjustable angles according to an embodiment of the present application, a first elastic arm and a second elastic arm extend from the second end of the angle block, and a first raised positioning platform and a second raised positioning platform are respectively provided on outer sides of the first elastic arm and the second elastic arm in a direction perpendicular to the rotation plane of the angle block, and the second ends of the first limiting plate and the second limiting plate are respectively provided with a first group of angle gear grooves and a second group of angle gear grooves for the first raised positioning platform and the second raised positioning platform being embedded therein respectively; and the elastic element abuts between the first elastic arm and the second elastic arm.

In the needle guiding bracket with adjustable angles according to an embodiment of the present application, the elastic element is a compression spring, and a first cylinder and a second cylinder are oppositely provided on inner side surfaces of the first elastic arm and the second elastic arm in a direction perpendicular to the rotation plane of the angle block, and two ends of the compression spring are respectively sleeved on the first cylinder and the second cylinder.

In the needle guiding bracket with adjustable angles according to an embodiment of the present application, angle gear marks corresponding to the first group of angle gear grooves and the second group of angle gear grooves are provided on outer surfaces of the first limiting plate and the second limiting plate respectively.

In the needle guiding bracket with adjustable angles according to an embodiment of the present application, the elastic arm is further provided with an operating portion to enable the raised positioning platform being released from the angle gear grooves.

In the needle guiding bracket with adjustable angles according to an embodiment of the present application, the mounting base is provided with a track block, and the track block has an undercut; and an elastic rail arm extends from the angle block opposite to the track block, and the elastic rail arm has an elastic barb which is just locked with the undercut when the angle block is rotated to a maximum angle relative to the mounting base.

In the needle guiding bracket with adjustable angles according to an embodiment of the present application, the elastic rail arm is further provided with a first sliding matching surface and a second sliding matching surface which are slidably matched with both sides of the track block during rotation of the angle block relative to the mounting base.

Implementing the needle guiding bracket with adjustable angles of the present application has the following beneficial effects: the needle guiding bracket according to embodiments of the present application achieves convenient angle adjustment by the elastic deformation of the elastic arms, prevents the loosening of angle positioning due to weakened elasticity of the elastic arms or accidental touch during an operation by elastic elements, has a simple structure, is convenient to operate, and has stable angle positioning.

BRIEF DESCRIPTION OF THE DRAWINGS

The present application will be further described with reference to the accompanying drawings and embodiments, in which:

FIG. 4 is a structural cross-sectional view of an angle block mounting on the mounting base according to an embodiment of the present application;

FIG. 5 is a structural cross-sectional view of the angle block shown in FIG. 4 being adjusted to a maximum angle;

DETAILED DESCRIPTION

To explain objects, technical solutions and advantages of the present application more clearly, the present application will be further described with reference to the accompanying drawings and embodiments in the following. It should be understood that, the specific embodiments described here are only for explanation, but not for limitation to the present application.

Figure 1:
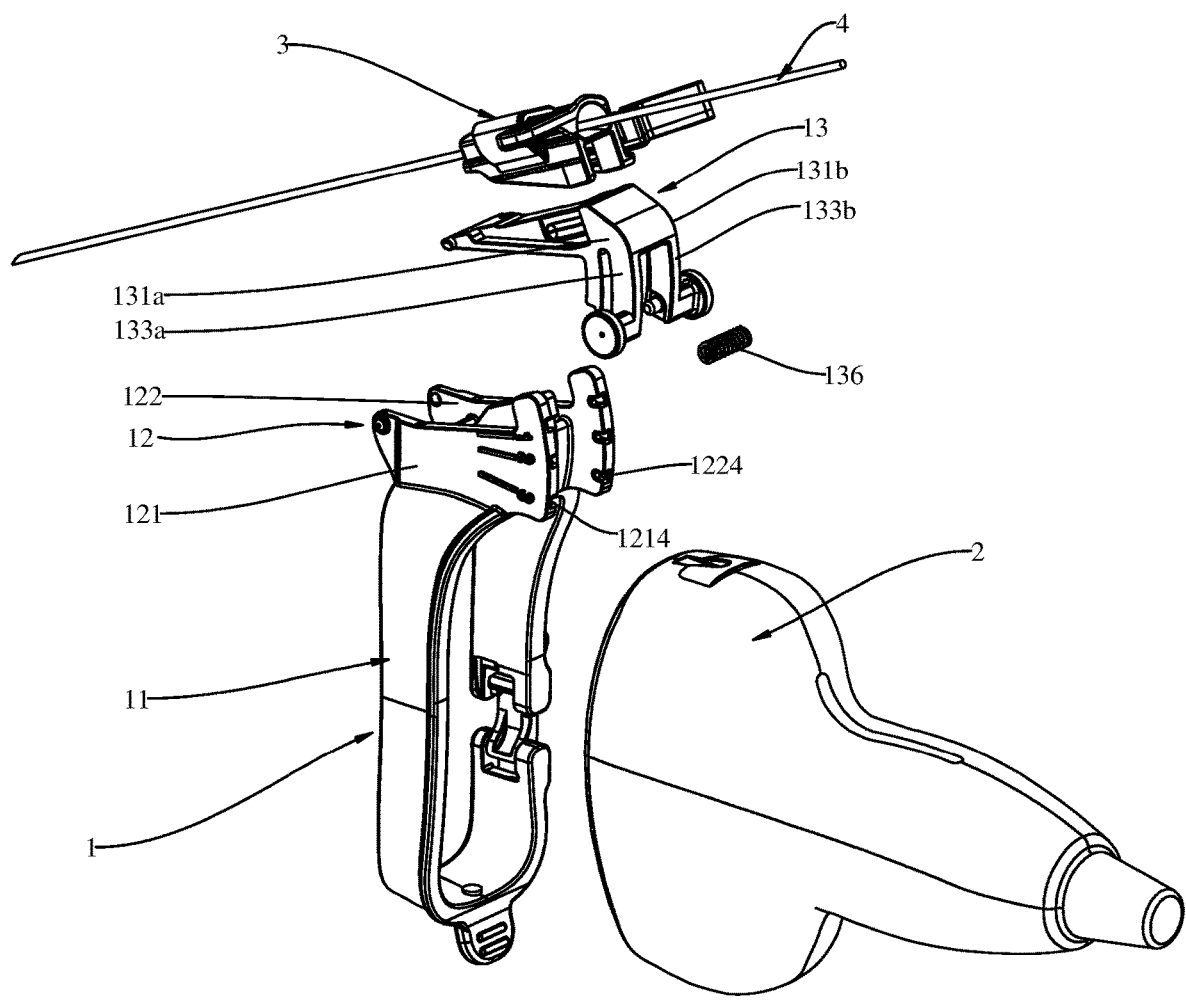
FIG. 1 is a schematic exploded structural diagram of a needle guiding bracket with adjustable angles in cooperation with an ultrasonic probe according to an embodiment of the present application.

FIG. 1 shows a schematic exploded structural diagram of a needle guiding bracket with adjustable angles in cooperation with an ultrasound probe according to an embodiment of the present application. As shown in FIG. 1, the needle guiding bracket 1 is installed onto the ultrasound probe 2, a needle guide 3 is installed onto the needle guiding bracket 1, and a needle 4 is guided via a needle tract of the needle guide 3 to perform a biopsy operation. The needle guiding bracket 1 comprises a bracket body 11, a mounting base 12 and an angle block 13. The bracket body 11 has configurations for cooperative mounting with the ultrasound probe 2, so that the needle guiding bracket 1 can be secured onto the ultrasound probe 2 without obvious shaking. The mounting base 12 is arranged on the bracket body 11 for rotary installation of the angle block 13. The mounting base 12 can be integrally provided with the bracket body 11. The angle block 13 and the mounting base 12 are rotationally connected at corresponding first ends, and a cooperating limiting structure is provided between the angle block 13 and the mounting base 12 to enable the angle block 13 and the mounting base 12 to only rotate relative to each other. The angle block 13 is also provided with configurations for mounting the needle guide 3, which can be realized by various existing or possible suitable technical means, and is not a concerned focus of the present application, so it will not be detailedly described here. The needle guide 3 is a needle guiding consumable, and provides the needle tract for guiding the needle 4. According to different embodiments of the present application, the needle guiding bracket can also be in the form of a needle tract being directly provided on the angle block, and the needle is guided via the needle tract on the angle block without additional equipment with a needle guide.

Figures 2, 3:
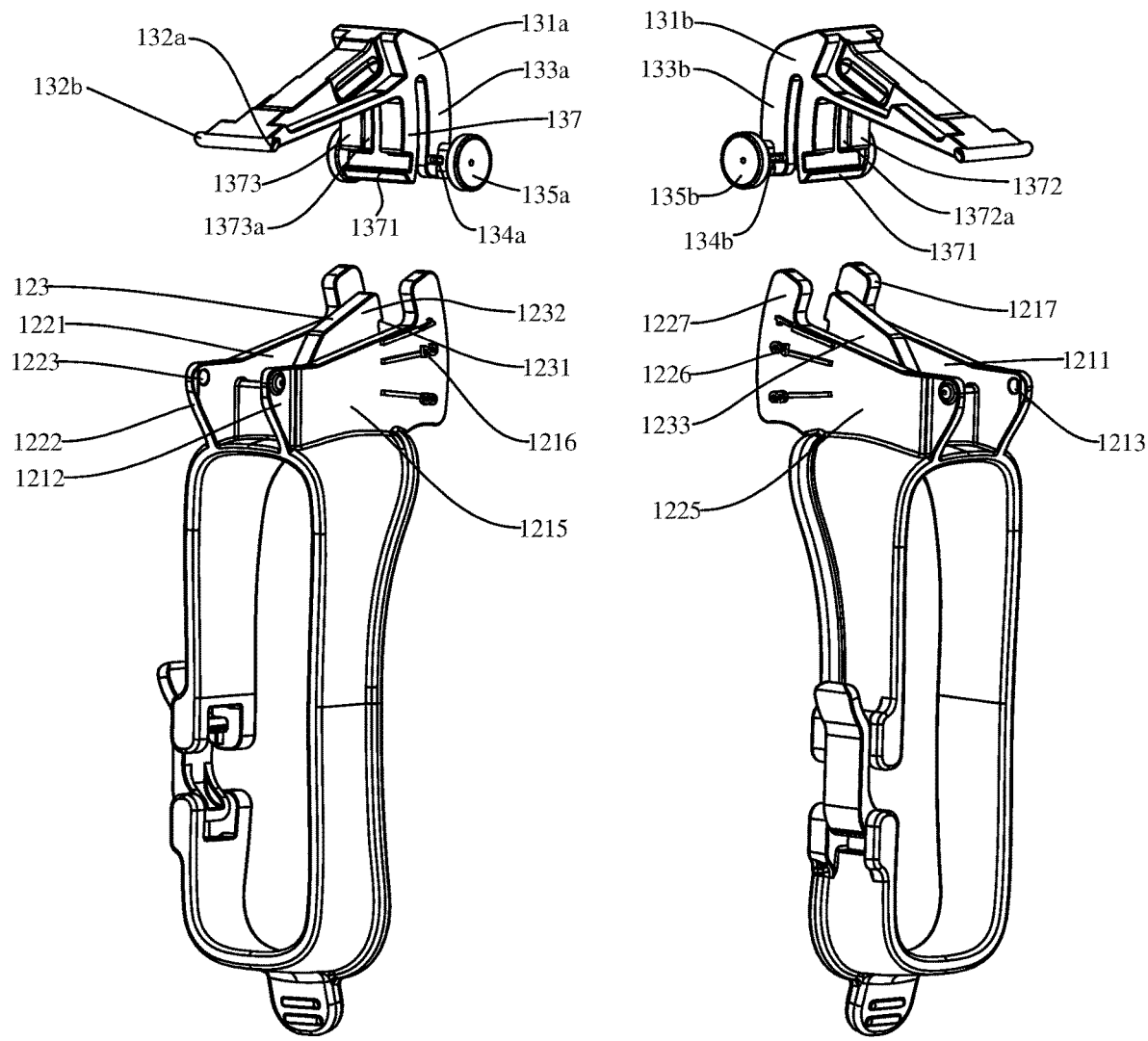
FIG. 2 is a schematic exploded structural diagram of a needle guiding bracket with adjustable angles according to an embodiment of the present application.
FIG. 3 is a schematic exploded structural diagram of the needle guiding bracket with adjustable angles as shown in FIG. 2 from another perspective view.
Figure 7:
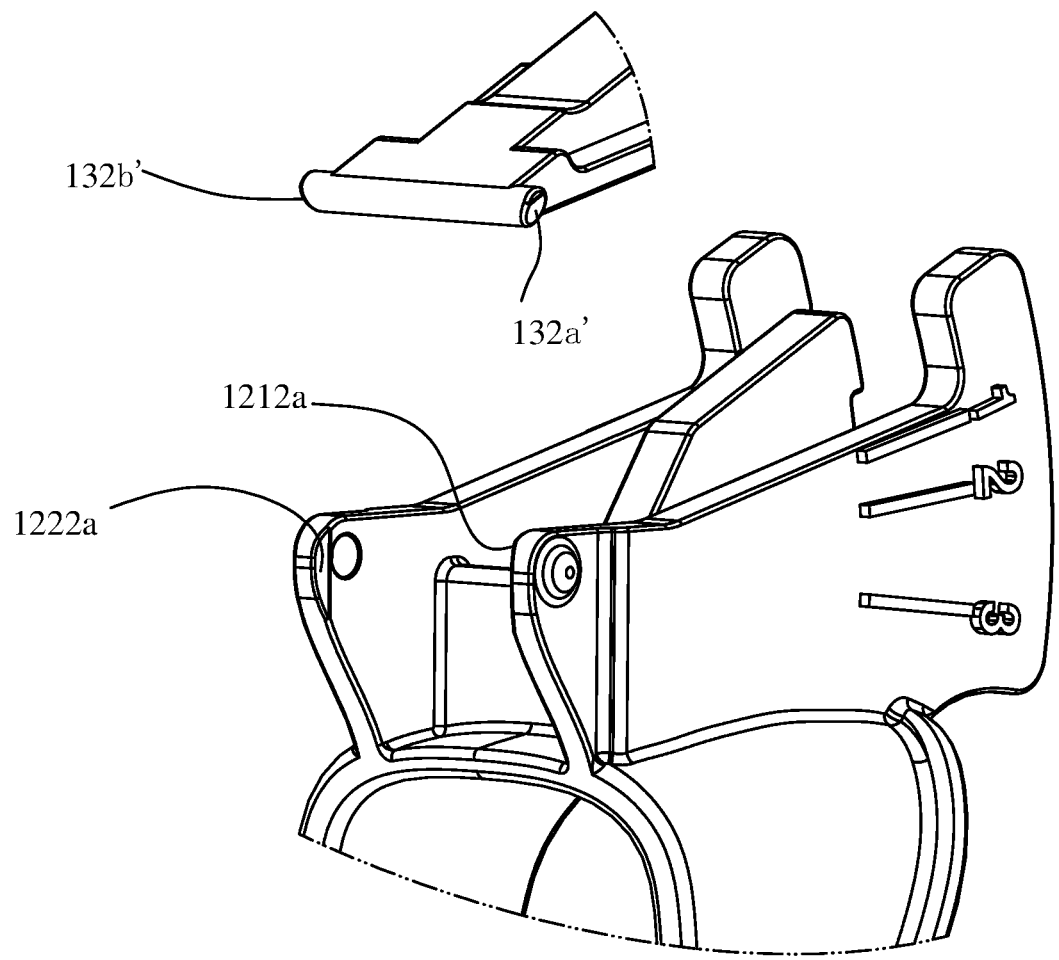
FIG. 7 is a partial structural schematic diagram of a rotatable connection between the angle block and the mounting base according to an embodiment of the present application.

Specifically, as shown in FIGS. 1, 2 and 3, the mounting base 12 comprises a first limiting plate 121 and a second limiting plate 122. A first elastic sheet 1212 and a second elastic sheet 1222 extend from the first ends of the first limiting plate 121 and the second limiting plate 122 respectively. The first elastic sheet 1212 and the second elastic sheet 1222 are correspondingly provided with a first mounting hole 1213 and a second mounting hole 1223. Two outer sides of a corresponding first end of the angle block 13 are respectively provided with a first rotating shaft 132a and a second rotating shaft 132b, which are installed into the first mounting hole 1213 and the second mounting hole 1223 so that the first end of the angle block 13 is rotationally connected between the first ends of the first limiting plate 121 and the second limiting plate 122. Specifically, as shown in FIG. 7, guide slopes 132a' and 132b' are respectively formed at the end of the first rotating shaft 132a and the second rotating shaft 132b, and guide slopes 1212a and 1222a are also respectively formed proximate the first mounting hole 1213 and the second mounting hole 1223 on the first elastic sheet 1212 and the second elastic sheet 1222. The first elastic sheet 1212 and the second elastic sheet 1222 can be deformed by cooperating extrusion between the two sets of guiding slopes 132a', 132b' and 1212a, 1222a, so that the first rotating shaft 132a and the second rotating shaft 132b can be installed into the first mounting hole 1213 and the second mounting hole 1223 to realize rotational connection.

As shown in FIGS. 1-3, the first limiting plate 121 has an inner surface 1211 and an outer surface 1215, and the second limiting plate 122 has an inner surface 1221 and an outer surface 1225. A first rotating matching surface 131a and a second rotating matching surface 131b are respectively provided on both sides of the angle block 13. The first rotating matching surface 131a and a second rotating matching surface 131b are cooperated with the inner surface 1221 of the first limiting plate 121 and the inner surface 1221 of the second limiting plate 122 respectively, and there is only a slight movable gap which enables the angle block 13 to only rotate relative to the mounting base 12.

Figure 6:
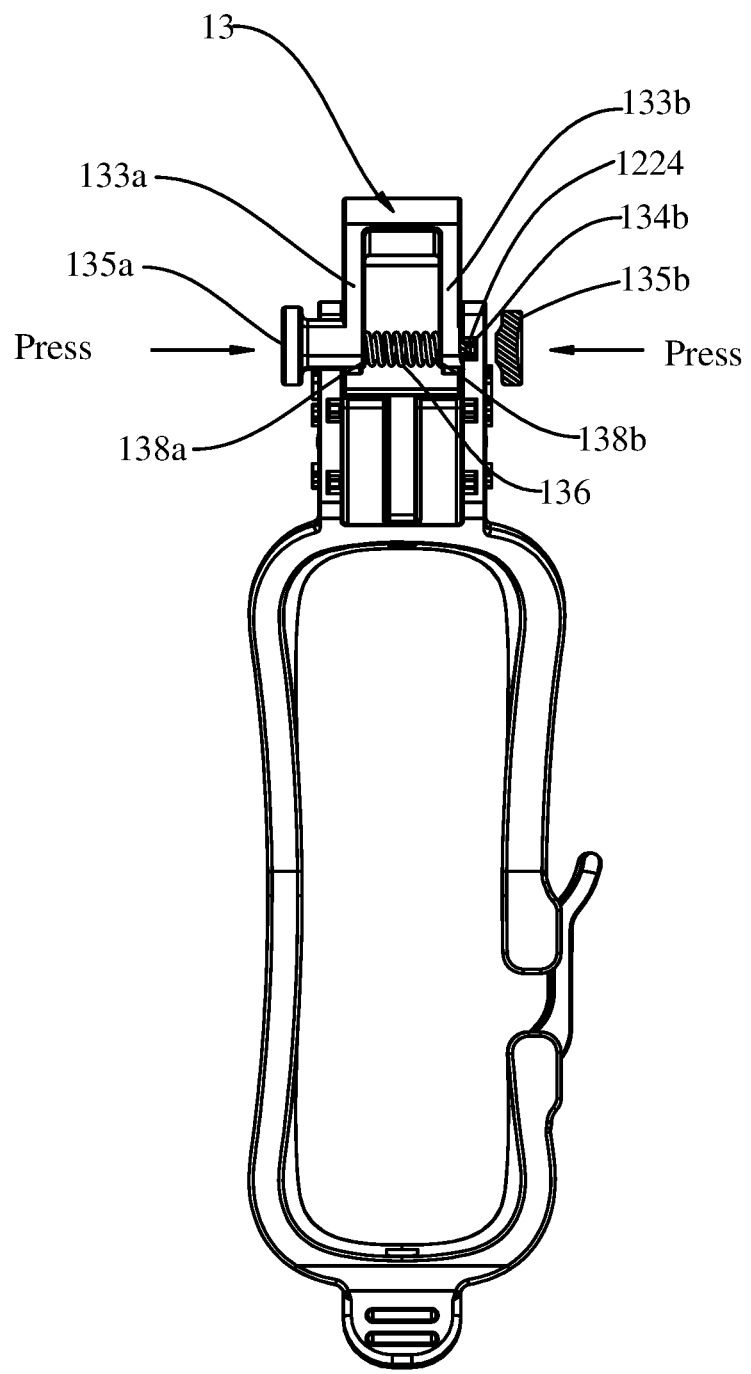
FIG. 6 is another structural cross-sectional view of the angle block shown in FIG. 5 being adjusted to a maximum angle.

Further as shown in FIGS. 1-3, a first elastic arm 133a and a second elastic arm 133b extend from a second end of the angle block 13 opposite to the first end. The first elastic arm 133a and the second elastic arm 133b are oppositely disposed on both sides of the second end of the angle block 13. In addition, a first raised positioning platform 134a and a second raised positioning platform 134b are respectively provided on outer sides of the first elastic arm 133a and the second elastic arm 133b in a direction perpendicular to a rotation plane of the angle block 13, and a first operating portion 135a and a second operating portion 135b are respectively provided on the first elastic arm 133a and the second elastic arm 133b close to the first raised positioning platform 134a and the second raised positioning platform 134b. A second end of the first limiting plate 121 is provided with a first group of angle gear grooves 1214 for the first raised positioning platform 134a to be embedded therein. Similarly, a second end of the second limiting plate 122 is provided with a second group of angle gear grooves 1224 for the second raised positioning platform 134b to be embedded therein. The first group of angle gear grooves 1214 and the second group of angle gear grooves 1224 each comprise at least two angle gear grooves distributed along a circumferential direction. For example, in the embodiment shown in FIG. 4, the second group of angle gear grooves 1224 comprises three angular gear grooves 1224a, 1224b and 1224c, as does the first group of angular gear grooves 1214. When the first raised positioning platform 134a and the second raised positioning platform 134b are respectively embedded within a corresponding angle gear groove 1214 and 1224, a fixed angle for biopsy operation can be formed between the angle block 13 and the mounting base 12. Referring to FIG. 6, when the angle for biopsy operation needs to be changed, the first operating portion 135a and the second operating portion 135b can be pressed by a user to make the first elastic arm 133a and the second elastic arm 133b elastically deform, so that the first raised positioning platform 134a and the second raised positioning platform 134b are respectively released from the corresponding angle gear grooves 1214 and 1224, then the angle block 13 can be rotated to another desired angle gear position, and then the pressing on the first operating portion 135a and the second operating portion 135b are released, the first elastic arm 133a and the second elastic arm 133b are restored, and the first raised positioning platform 134a and the second raised positioning platform 134b can be inserted into another corresponding angle gear groove 1214 and angle gear groove 1224 again, and angle adjustment and positioning is realized. In order to facilitate a doctor to select an angle for biopsy operation, angle gear marks 1216 and 1226 corresponding to the first group of angle gear grooves 1214 and the second group of angle gear grooves 1224 are provided on the outer surface 1215 of the first limiting plate 121 and the outer surface 1225 of the second limiting plate 122 respectively, by means of which the doctor can align a desired angle for biopsy operation conveniently.

Because the needle guiding bracket 1 is used as a reusable instrument in the hospital, it needs to be sterilized after each use, and its service life needs to meet the requirements of long-term multiple use. However, the first elastic arm 133a and the second elastic arm 133b have relatively small elastic forces, which may weaken or even fail during long-term use. Moreover, there is a risk of releasing of angle positioning during use caused by mistakenly pressing the first operating portion 135a and the second operating portion 135b. Therefore, the angle block 13 is also provided with an elastic element 136, which is configured to apply elastic force to the first elastic arm 133a and the second elastic arm 133b to urge the first raised positioning platform 134a and the second raised positioning platform 134b to be embedded in the corresponding angle gear grooves 1214 and 1224. Referring specifically to the embodiment shown in FIG. 6, the elastic element 136 is a compression spring, a first cylinder 138a and a second cylinder 138b are oppositely provided on inner side surfaces of the first elastic arm 133a and the second elastic arm 133b in a direction perpendicular to the rotation plane of the angle block 13, and two ends of the compression spring 136 are respectively sleeved on the first cylinder 138a and the second cylinder 138b. The compression spring 136 is in a contracted state, providing stronger and lasting support for the first elastic arm 133a and the second elastic arm 133b, so that the first raised positioning platform 134a and the second raised positioning platform 134b are embedded in the corresponding angle gear grooves 1214 and 1224 and are not easy to be released. When the angle for biopsy operation needs to be changed, pressing the first operating portion 135a and the second operating portion 135b from both sides of the angle block 13 to the middle at the same time, makes the first elastic arm 133a, the second elastic arm 133b and the compression spring 136 to deform together, bringing the first raised positioning platform 134a and the second raised positioning platform 134b being released from the corresponding angle gear grooves 1214 and 1224. Then the angle block 13 is rotated to make the first raised positioning platform 134a and the second raised positioning platform 134b align with the angle gear grooves 1214 and 1224 of a desired needle guiding angle, and then the pressing on the first operating portion 135a and the second operating portion 135b is released, the first operating portion 135a, the second operating portion 135b and the compression spring 136 deform and rebound, so that the first raised positioning platform 134a and the second raised positioning platform 134b are respectively embedded in the angle gear grooves 1214 and 1224 of the adjusted needle guiding angle. Then angle adjustment and positioning is completed. According to different embodiments of the present application, the elastic element 136 may also adopt other elements other than the compression spring, such as a torsion spring, as long as elastic forces can be applied to the elastic arms 133a, 133b to urge the raised positioning platforms 134a, 134b to be embedded in the angle gear grooves 1214, 1224. Depending on types of the elastic element used, installation structure of the elastic element can also be changed correspondingly. In the illustrated embodiment, the elastic arms, the raised positioning platforms and the operating portions on the angle block 13 are arranged in pairs, which is easier to adjust the angle, and the two raised positioning platforms can also prevent the angle positioning from being released by mistakenly pressing the operating portions during the operation. However, according to different embodiments of the present application, only a set of an elastic arm, a raised positioning platform and an operation portion are provided on the angle block to cooperate with a group of angle gear grooves correspondingly provided on the mounting base, and the angle adjustment and positioning can also be realized.

Further referring to FIG. 2 and FIG. 3 in combination with FIG. 5, in order to limit an over-range rotation of the angle block 13 during the adjustment of the needle guiding angle, the mounting base 13 is further provided with a track block 123, and the track block 123 has an undercut 1231. An elastic rail arm 137 extends from the angle block 13 opposite to the track block 123. The elastic rail arm 137 has an elastic barb 1371, and the elastic barb 1371 can elastically lock into the undercut 1231 of the track block 123. During angle adjustment, when the angle block 13 is rotated to a maximum angle relative to the mounting base 12, as shown in FIG. 5, the elastic barb 1371 is just locked with the undercut 1231 to provide position limitation, thereby restricting the angle block 13 only rotating within a required rotation range, thus the angle block 13 cannot fall out of the mounting base 12. At the same time, when the needle guiding angle is adjusted to the maximum angle, positioning stability of the angle block 13 will become lower and it is easier to shake because rotation matching areas between the angle block 13 and the first limiting plate 121 and the second limiting plate 122 become smaller. To this end, the elastic rail arm 137 is provided with a first protrusion 1372 and a second protrusion 1373, and two inner surfaces of the first protrusion 1372 and the second protrusion 1373 opposite to each other form a first sliding matching surface 1372a and a second sliding matching surface 1373a which are slidably matched with both sides of the track block 123 to enhance the positioning stability of the angle block 13. In addition, a first extension plate 1217 and a second extension plate 1227 are additionally provided at the second ends of the first limiting plate 121 and the second limiting plate 122. Inner sides of the first extension plate 1217 and the second extension plate 1227 cooperate with the first rotating matching surface 131a and the second rotating matching surface 131b of the angle block 13 to increase limitation and ensure the stability of angle positioning.

The above is only the preferred embodiments of the present application, and is not intended to limit the present application. Any modifications, equivalent substitutions and improvements made within the spirit and principles of the present application should be included within the protection scope of the present application.

What is claimed is:

1. A needle guiding bracket with adjustable angles, comprising a bracket body configured to cooperatively mount with an ultrasound probe, a mounting base arranged on the bracket body, and an angle block rotationally connected with the mounting base, wherein the angle block and the mounting base are rotationally connected at corresponding first ends, and a corresponding limiting structure is provided between the angle block and the mounting base to enable the angle block and the mounting base to only rotate relative to each other, and the angle block is also provided with configurations for mounting a needle guide or directly forming a needle tract, characterized in that:

the mounting base comprises a first limiting plate and a second limiting plate, and the first end of the angle block is rotationally connected between the first ends of the first limiting plate and the second limiting plate;

a first elastic arm and a second elastic arm extend from a second end of the angle block, and a first raised positioning platform and a second raised positioning platform are respectively provided on outer sides of the first elastic arm and the second elastic arm in a direction perpendicular to the rotation plane of the angle block, and corresponding second ends of the first limiting plate and the second limiting plate are respectively provided with a first group of angle gear grooves and a second group of angle gear grooves for the first raised positioning platform and the second raised positioning platform being embedded therein respectively;

the angle block is further provided with an elastic element which abuts between the first elastic arm and the second elastic arm and applies elastic force to the first elastic arm and the second elastic arm to urge the first raised positioning platform and the second raised positioning platform to be embedded within the corresponding angle gear grooves, wherein the elastic element is a compression spring, and a first cylinder and a second cylinder are oppositely provided on inner side surfaces of the first elastic arm and the second elastic arm in a direction perpendicular to the rotation plane of the angle block, and two ends of the compression spring are respectively sleeved on the first cylinder and the second cylinder; and the mounting base is provided with a track block positioned between the first limiting plate and the second limiting plate, and the track block has an undercut; and an elastic rail arm extends from the angle block opposite to the track block, and the elastic rail arm has an elastic barb which is just locked with the undercut when the angle block is rotated to a maximum angle relative to the mounting base.

2. The needle guiding bracket with adjustable angles of claim 1, wherein a first elastic sheet and a second elastic sheet extend from the first ends of the first limiting plate and the second limiting plate respectively, with the first elastic sheet and the second elastic sheet being correspondingly provided with a first mounting hole and a second mounting hole, and two outer sides of the first end of the angle block are respectively provided with a first rotating shaft and a second rotating shaft which are installed into the first mounting hole and the second mounting hole.

3. The needle guiding bracket with adjustable angles of claim 1, wherein a first rotating matching surface and a second rotating matching surface are respectively provided on both sides of the angle block, and the first rotating matching surface and the second rotating mating surface respectively cooperate with an inner surface of the first limiting plate and an inner surface of the second limiting plate to limit the angle block and the mounting base to only rotate relative to each other.

4. The needle guiding bracket with adjustable angles of claim 1, wherein angle gear marks corresponding to the first group of angle gear grooves and the second group of angle gear grooves are provided on outer surfaces of the first limiting plate and the second limiting plate respectively.

5. The needle guiding bracket with adjustable angles of claim 1, wherein each of the first elastic arm and the second elastic arm is further provided with an operating portion to enable the raised positioning platform being released from the angle gear grooves.

6. The needle guiding bracket with adjustable angles of claim 1, wherein the elastic rail arm is further provided with a first sliding matching surface and a second sliding matching surface which are slidably matched with both sides of the track block during rotation of the angle block relative to the mounting base.

* * * * *